United States Patent [19]

Kaplan et al.

[11] Patent Number: 5,095,011

[45] Date of Patent: Mar. 10, 1992

[54] LYOPHILIZED CEFEPIME DIHYDROCHLORIDE FOR PARENTERAL USE

[75] Inventors: Murray A. Kaplan, Syracuse; Munir N. Nassar, Manlius, both of N.Y.

[73] Assignee: Bristol-Myers Company, New York, N.Y.

[21] Appl. No.: 631,751

[22] Filed: Dec. 20, 1990

Related U.S. Application Data

[63] Continuation of Ser. No. 318,985, Mar. 6, 1989, abandoned.

[51] Int. Cl.$^5$ ............... C07D 501/00; C07D 501/14; A61K 31/545
[52] U.S. Cl. ..................... 514/202; 540/222
[58] Field of Search ............ 514/202; 540/222

[56] References Cited

U.S. PATENT DOCUMENTS

| | | | |
|---|---|---|---|
| 4,406,899 | 9/1983 | Aburaki et al. | 514/202 |
| 4,808,617 | 2/1989 | Kaplan et al. | 514/202 |
| 4,910,301 | 3/1990 | Kaplan et al. | 540/222 |

*Primary Examiner*—Frederick E. Waddell
*Assistant Examiner*—Raymond J. Henley, III
*Attorney, Agent, or Firm*—Aldo A. Algieri

[57] ABSTRACT

A stable, amorphous, lyophilized dihydrochloride salt of 7-[α-(2-aminothiazol-4-yl)-α-(z)-methoxyiminoacetamido]-3-[(1-methyl-1-pyrrolidinium) methyl]-3-cephem-4-carboxylate is described. This lyophilized salt is more easily prepared than the crystalline counterpart and can be reconstituted in effective concentrations for intramuscular and intravenous injection utilizing suitable organic and inorganic bases to pH 3-7.0.

3 Claims, No Drawings

LYOPHILIZED CEFEPIME DIHYDROCHLORIDE FOR PARENTERAL USE

This application is a continuation of application Ser. No. 07/318,985, filed Mar. 6, 1989, now abandoned.

TECHNICAL FIELD

This invention is directed to the stable, lyophilized, amorphous, dihydrochloride of 7-[α-(2-aminothiazol-4-yl)-α-(Z)-methoxyiminocetamido]-3-[(1-methyl-1-pyrrolidinium)methyl]-3-cephem-4-carboxylate (BMY-28142, cefepime) which may be reconstituted with aqueous vehicles containing suitable organic and inorganic bases, affording parenteral solutions with effective concentrations of BMY-28142 activity.

BACKGROUND OF INVENTION

Aburaki et al U.S. Pat. No. 4,406,899 discloses BMY-28142 in zwitterionic form and its acid addition salts (in zwitterionic form in injectable compositions). This amorphous zwitterionic form shows broader spectrum activity than ceftazidime and cefotaxime but may require special packaging and/or refrigeration.

Various crystalline acid addition salts of BMY-28142 are disclosed in U.S. Ser. No. 144,899 filed Jan. 19, 1988. These crystalline salts are the sulfuric, di-nitric, monohydrochloric, and di-hydrochloric acid salts and orthophosphoric acid addition salts (from 1.5 to 2 moles of orthophosphoric acid per mole of BMY-28142). These crystalline salts, while possessing better temperature stability in dry powder form than the amorphous zwitterion, require formulation with bases and/or buffering agents for aqueous constitution because they are too acidic for use either intramuscularly or intravenously. Combinations of various salts in either a lyophilized or precipitated form with BMY-28142 are disclosed in U.S. Ser. No. 001,945 filed Jan. 9, 1987 and/or G.B. Patent application No. 2,199,746A. These combinations are formed by lyophilization or cosolvent precipitation of an aqueous solution of the zwitterion of BMY-28142 and one or more salts in which said salts have sodium, lithium, calcium or magnesium cations and chloride, bromide or iodide anions. These combinations have improved temperature stability in dry powder form over the zwitterion in injectable form and while they provide, upon dilution, injectable concentrations at pH 3.5-7 without the need for any other buffering agents or bases, their stability is not as good as the crystalline salts.

SUMMARY OF THE INVENTION

The present invention is directed to a stable, amorphous, lyophilized form of 7-[α-(2-aminothiazol-4-yl)-α-(Z)-methoxyiminoacetamido]-3-[(1-methyl-1-pyrrolidinium) methyl]-3-cephem-4-carboxylate, namely, its dihydrochloride salt. The structure of this compound is as follows:

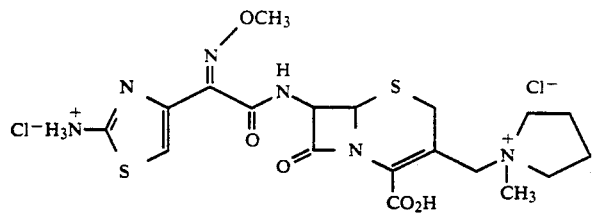

U.S. Pat. No. 4,406,899 discloses the broad spectrum utility of the zwitterion form against various organisms. The crystalline form of this compound is disclosed in U.S. Ser. No. 144,899 filed Jan. 19, 1988.

The present invention, however, supplies an alternative stable form of this compound, that is, the lyophilized form. The amorphous dihydrochloride salt is unexpectedly stable and therefore permits its preparation where manufacturing facilities do not permit the preparation of the crystalline dihydrochloride salt. This lyophilized preparation of the dihydrochloride permits simpler dosage forms than the zwitterion di-(1-methyl-pyrrolidinone-2) adducts (U.S. Pat No. 4,680,389) or combinations of the zwitterion and various salts (U.S. Ser. No. 001,945, filed Jan. 9, 1987).

DETAILED DESCRIPTION OF THE INVENTION

The amorphous, lyophilized, stable dihydrochloride form 7-[α-(2-aminothiazol-4-yl)-α-(Z)-methoxyiminoacetamido]-3-[(1-methyl-1-pyrrolidinium) methyl]-3-cephem-4-carboxylate (BMY-28142) of the present invention affords a convenient alternative source of this broad spectrum antibiotic. It has been found that the amorphous dihydrochloride salt of this lyophile is unexpectedly more stable than the lyophilized, amorphous sesqui-$H_3PO_4$, mono-$H_2SO_4$ and mono-HCl salts.

The manufacture of the crystalline form of this compound requires special plant facilities and is more costly to produce both in the amount of time needed and in the cost of materials and solvents.

Aburaki et al. U.S. Pat. No. 4,406,899 discloses a method for synthesizing BMY-28142 and also teaches the preparation of BMY-28142 in amorphous zwitterionic form as well as some of its acid addition salts. These compounds show broad spectrum activity. However, the compounds have limited stability (only a few hours) as injectable compositions. Even the dry powder is unstable at room temperature and can lose 30% or more of its activity when stored at elevated temperatures (e.g. 45° C. and above) for even one week.

In contrast, the lyophilized compound of the present invention is simple to prepare and is more stable.

A general procedure for the preparation of the amorphous dihydrochloride involves the mixing of the zwitterion (BMY-28142) with sufficient dilute hydrochloric acid to provide 2 moles thereof, and then lyophilizing the solution at reduced pressures and temperatures. The lyophilized amorphous sesqui-$H_3PO_4$, mono-HCl and mono-$H_2SO_4$ salts were also prepared by similar procedures and were also tested for stability. Surprisingly, the only salt which showed unusual and unexpected stability with commercial potential was the lyophilized amorphous dihydrochloride salt of BMY-28142. Stability test results of these compounds are shown in Table II, below.

Crystalline acidic salts, such as the di-HCl, sesqui-H₃PO₄ and H₂SO₄ salts, while also temperature stable, are too acidic for intramuscular and intravenous use alone, and require buffering to physiologically acceptable pH ranges by, for example, the use of various organic and inorganic bases, before they can be administered.

U.S. Ser. No. 001,945 or G.B. Patent Application No. 2,199,746A discloses a combination of a salt lyophilized with, or coprecipitated with the zwitterion of BMY-28142. The salts are those containing sodium, lithium, calcium and magnesium cations and chloride, bromide or iodide anions, and are coprecipitated or lyophilized with the BMY-28142 zwitterion. These compositions, while being more stable than the zwitterion acid addition salts in injectable form disclosed in U.S. Pat. No. 4,406,899 and not requiring further pH adjustment before injection, are not as stable as the crystalline BMY-28142 salts.

Of course, any of the disadvantages of the prior art can be eliminated by using a 2-vial system wherein one vial contains the dry-fill deposited crystalline salt and the other vial has the correct concentration of the organic or inorganic base as a solid or in aqueous solution. The required amount of base solution (vial 2) can be added to the vial containing the crystalline salts (vial 1) which results in the desired pH and concentration of BMY-28142 salt solution.

It is with regard to the use of a sterile dry-fill of BMY-28142 crystalline salt in a 2-vial system that the lyophilized dihydrochloride of BMY-28142 shows to advantage. This is so since the lyophilized counterpart is a simpler and more desirable physical form in this instance than the crystalline form and requires minimal equipment and no solvents, thus being more cost effective than its crystalline counterpart.

In essence, the present invention provides for an unexpected, particularly stable, lyophilized amorphous dihydrochloride salt of BMY-28142. This salt may be lyophilized in vial and can be reconstituted with various aqueous vehicles containing organic and inorganic bases to pH 3-7.0.

These bases can be, for example lysine, arginine, N-methylglucamine, tris(hydroxymethyl)aminomethane (TRIS), sodium bicarbonate, sodium carbonate, sodium dihydrogen phosphate, disodium hydrogen phosphate, trisodium phosphate and the like to provide for parenteral (IM-IV) solutions at pH 3-7.0 and at concentrations of up to 400 mg/ml of BMY-28142 activity. Of course, the potassium (and other anion) salts can be used in place of these sodium salts, where indicated. Preparation of BMY-28142-2HCl in lyophilized form is described below. Additionally, the mono HCl sesquiphosphate and mono-di-hydrogen sulfate salts were prepared and the stabilities of these lyophilized acid addition salts were compared. The surprising and unexpected stability of the lyophilized dihydrochloride salt as compared to other lyophilized acid salts is shown in Table I. Based on these tests, it is expected that lyophilized BMY-28142 dihydrochloride would have shelf life of at least 12 months at room temperature and at least 24 months at 4° C.

As is shown in Tables II and III reconstitution with, for example, L(+)-arginine results in a utility time of 48 hours at 4° C. and about 12 hours at 25° for the reconstituted solutions, which provide adequate stability times for daily use.

EXAMPLE I

Lyophilization of BMY 28142 Dihydrochloride 0.5 Gram of BMY-28142 Zi was dissolved qs to 33 ml with 1.9 ml of 1N-HCl and water for injection (pH=2.0).

One ml portion (approximately 65 mg/ml) of the solution were placed into 10cc flint vials which were loosely stoppered with split lyphlization stoppers, frozen to −40° C. and lyphilized at a shelf temperature of 0° C. for 24 hours, then at 24° C. for 24 hours and at 32.2° C. for four hours. The vials were then sealed with aluminum closures and tested for stability at 56°, 45° and 37° C.

The results of these tests can be found in Table I.

TABLE I

Stability of Lyophilized Amorphous BMY-28142 Dihydrochloride and other Lyophilized Amorphous Salts

| Time-Temperature | % Remaining Salt | | | |
|---|---|---|---|---|
| | Di-HCl | Mono-HCl | Sesqui-PO₄ | Mono-H₂SO₄ |
| 4 Weeks-37° C. | 98.6 | 88.5 | 83.4 | 89.4 |
| 6 Weeks-37° C. | (97.2)* | — | 79 | 82 |
| 13 Weeks-37° C. | 95.5 | | | |
| 41 Weeks-37° C. | 91.7 | | | |
| 1 Week-45° C. | 99.8 (100) | 93.6 | 86.8 | 83.9 |
| 2 Weeks-45° C. | 97.2 | — | 80 | — |
| 4 Weeks-45° C. | 96 (92.5) | 79.4 | 74.3 | 78.6 |
| 13 Weeks-45° C. | 91.6 | | | |
| 26 Weeks-45° C. | 87.7 | | | |
| 1 Week-56° C. | (96) | — | 75 | 82.7 |
| 2 Weeks-56° C. | (91.8) | — | 61.9 | 72.2 |
| 4 Weeks-56° C. | 92.6 | 63.6 | | |
| 8 Weeks-56° C. | 87 | | | |
| 6 Months-25° C. | (100) | | | |
| 41 Weeks-25° C. | 98.1 | | | |
| 52 Weeks-25° C. | (100) | — | 63.6 | 64.8 |

*( ) second lot, separately prepared

TABLE II

Solution Stability of BMY-28142 DiHCl + L(+)-Arginine
Following Constitution with Water for Injection to 250 mg Base/ml
(pH ~5) at 4° C. and 25° C.

| Sample No. | Temp. (°C.) | Initial BMY-28142 % Remaining | pH | % NMP | 6 hr BMY-28142 % Remaining | pH | % NMP[a] | 24 hr BMY-28142 % Remaining | pH | % NMP[a] | 48 hr BMY-28142 % Remaining | pH | % NMP[a] |
|---|---|---|---|---|---|---|---|---|---|---|---|---|---|
| 1 | 4  | 100.0 | 5.4 | — | 99.0 | —   | 0.5  | 98.4 | 6.0 | 0.5  | 96.7 | 5.5 | 0.6 |
|   | 25 | 100.0 | —   | — | 97.2 | 5.4 | 0.6  | 91.0 | —   | 1.0  | 83.6 | 5.2 | 1.8 |
| 2 | 4  | 100.0 | —   | — | 99.1 | —   | 0.1  | 98.2 | —   | 0.4  | 96.5 | 5.7 | 0.2 |
|   | 25 | 100.0 | —   | — | 97.3 | 5.4 | 0.3  | 91.1 | 5.4 | 0.95 | 83.5 | 5.3 | 1.7 |
| 3 | 4  | 100.0 | —   | — | 99.6 | —   | 0.4  | 97.0 | —   | 0.6  | 95.8 | 6.1 | 0.4 |
|   | 25 | 100.0 | —   | — | 97.0 | —   | 0.5  | 90.0 | 5.5 | 1.2  | 83.2 | 5.9 | 2.0 |

[a]NMP = N-methylpyrrolidine (degradation product) as determined via NMR.

TABLE III

Solution Stability of BMY-28142 DiHCl + L(+)-Arginine Following Constitution with
Water for Injection to 325 mg Activity/mL at 4° C. and 25° C.

| Temp. (°C.) | Time (hours) | BMY-28142 Conc.[a] (mg/mL) | NMP[a] (% w/w) | Klett | pH | Impurities[a] (Area %) | Physical Observation[a] |
|---|---|---|---|---|---|---|---|
| 4  | 0  | 318 | 0.53 | 280 | 4.89 | None observed | Clear, yellow solution |
|    | 6  | 324 | 0.45 | 300 | 4.89 | None observed | Clear, yellow solution |
|    | 24 | 322 | 0.45 | 345 | 4.85 | None observed | Clear, yellow solution |
|    | 48 | 308 | 0.35 | 360 | 4.73 | None observed | Clear, yellow solution |
| 25 | 0  | 324 | 0.52 | 292 | 4.82 | None observed | Clear, yellow solution |
|    | 6  | 318 | 0.63 | 340 | 4.76 | None observed | Clear, medium yellow solution |
|    | 24 | 296 | 1.31 | 410 | 4.72 | None observed | Clear, dark yellow solution |

[a]NMP = N-methylpyrrolidine (degradation product) as determined via NMR.

EXAMPLE II

In a similar manner to Example I, but using the appropriate acid in the required amounts, the dihydrochloride, monohydrochloride, sesquiphosphate and mono sulfate salts of BMY-28142 were prepared and lyophilized. The stabilities of these amorphous lyophilized salts compared to the dihydrochloride salt is also shown in Table I.

EXAMPLE III 375 mg L(+)-Arginine for injection is reconstituted with 4.45 ml of sterile water for injection. The solution is taken up in a syringe and is added to a vial containing lyophilized BMY-28142-2HCl having an activity of 500 mg activity per vial. This solution produces a reconstituted solution suitable for injection which has an activity of about 100 mg BMY-28142 per milliliter.

Control of the amount of water used for dilution permitted the attainment of high concentrations up to 400 mg BMY-28142 per ml.

We claim:

1. A stable, lyophilized, amorphous dihydrochloride salt of 7-[α-(2-aminothiazol-4-yl)-α-(Z)-methoxyiminoacetamido]-3-[(1-methyl-1-pyrrolidinium)methyl]-3-cephem-4-carboxylate having the formula

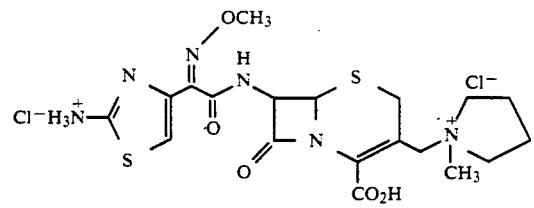

2. A reconstituted, injectable composition which comprises an effective antibacterial amount of the compound defined in claim 1 in an aqueous solution having a suitable organic or inorganic base wherein the pH of the resulting solution is between 3 and 7.0 with concentrations up to 400 mg/ml of active ingredient.

3. The reconstituted, injectable composition according to claim 2 wherein the base is selected from the group consisting of lysine, arginine, N-methylglucamine, tris(hydroxymethyl)aminomethane, $NaHCO_3$, $Na_2CO_3$, $NaH_2PO_4$, $Na_2HPO_4$, $Na_3PO_4$, $KHCO_3$, $K_2CO_3$, $KH_2PO_4$, $K_2HPO_4$ and $K_3PO_4$.

* * * * *